(12) United States Patent
Margulies et al.

(10) Patent No.: US 11,471,454 B2
(45) Date of Patent: Oct. 18, 2022

(54) METHODS AND COMPOSITIONS FOR TREATING CANCER

(71) Applicant: Zetagen Therapeutics, Inc., Syracuse, NY (US)

(72) Inventors: Bryan S. Margulies, Liverpool, NY (US); Nikhil A. Thakur, Andover, MA (US)

(73) Assignee: Zetagen Therapeutics, Inc., Syracuse, NY (US)

(*) Notice: Subject to any disclaimer, the term of this patent is extended or adjusted under 35 U.S.C. 154(b) by 0 days.

(21) Appl. No.: 17/219,394

(22) Filed: Mar. 31, 2021

(65) Prior Publication Data

US 2021/0228571 A1    Jul. 29, 2021

Related U.S. Application Data

(63) Continuation of application No. 16/928,830, filed on Jul. 14, 2020, now abandoned.

(60) Provisional application No. 62/874,037, filed on Jul. 15, 2019.

(51) Int. Cl.
| | |
|---|---|
| *A61K 31/485* | (2006.01) |
| *A61P 35/00* | (2006.01) |
| *A61K 9/00* | (2006.01) |
| *A61K 47/20* | (2006.01) |
| *A61K 47/42* | (2017.01) |

(52) U.S. Cl.
CPC .......... *A61K 31/485* (2013.01); *A61K 9/0019* (2013.01); *A61K 47/20* (2013.01); *A61K 47/42* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,882,944 A | 3/1999 | Sadee | |
| 6,007,986 A | 12/1999 | Sadee | |
| 6,270,979 B1 | 8/2001 | Sadee | |
| 6,384,044 B1 | 5/2002 | Bihari | |
| 6,713,488 B2 | 3/2004 | Sadee et al. | |
| 6,737,397 B1* | 5/2004 | Zagon | A61K 31/485 604/892.1 |
| 2007/0197573 A1 | 8/2007 | Sadee et al. | |
| 2010/0286059 A1 | 11/2010 | Moss et al. | |
| 2017/0286630 A1 | 10/2017 | Wong et al. | |

FOREIGN PATENT DOCUMENTS

| | | |
|---|---|---|
| WO | WO-2015/184059 A1 | 12/2015 |
| WO | WO-2015/189597 A1 | 12/2015 |
| WO | WO-2016/061531 A1 | 4/2016 |
| WO | WO-2019/246353 A1 | 12/2019 |

OTHER PUBLICATIONS

McLaughlin et al., International Journal of Oncology (2004), 24(1), pp. 227-232.*
Bimonte et al., OncoTargets and Therapy (2018), 11, pp. 185-191.*
McLaughlin et al., Expert Review of Anticancer Therapy (2014), 14(3), pp. 247-250.*
Bimonte et al., In Vivo (May-Jun. 2019), 33(3), pp. 821-825.*
Komuro et al., Journal of Controlled Release (2013), 168(3), pp. 298-306.*
Migotto et al., Drug Delivery (2018), 25(1), pp. 654-667.*
Hytrek et al., "Inhibition of human colon cancer by intermittent opioid receptor blockade with naltrexone," Cancer Letters, Mar. 1, 1996, 101(2);159-164.
Phosphate Buffered Saline Product Page (ThermoFisher Scientific). Published 2020 (Year: 2020). (7 pages).

* cited by examiner

*Primary Examiner* — Brian J Davis
(74) *Attorney, Agent, or Firm* — Foley & Lardner LLP

(57) ABSTRACT

This disclosure relates to methods and compositions for treating cancer by administering opioid growth factor receptor (OGFR) antagonists. In particular, the present disclosure relates to methods of administering OGFR antagonists locally to the site of cancer cells in the patient diagnosed with cancer.

20 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      OGFR binding antagonist"

<400> SEQUENCE: 1

Tyr Gly Gly Phe Met
1               5

<210> SEQ ID NO 2
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      OGFR binding antagonist"

<400> SEQUENCE: 2

Tyr Gly Gly Phe Leu
1               5

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Aminoisobutyticacid

<400> SEQUENCE: 3

Tyr Xaa Xaa Phe Leu
1               5

<210> SEQ ID NO 4
```

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (7)..(7)
<223> OTHER INFORMATION: Pen

<400> SEQUENCE: 4

Xaa Cys Tyr Xaa Lys Thr Xaa Thr
1               5

<210> SEQ ID NO 5
<211> LENGTH: 50
<212> TYPE: PRT
<213> ORGANISM: Unknown
<220> FEATURE:
<221> NAME/KEY: source
<223> OTHER INFORMATION: /note="Description of Unknown:
      OGFR antagonist"

<400> SEQUENCE: 5

Gln Ser Ala Leu Asp Tyr Phe Met Phe Ala Val Arg Cys Arg His Gln
1               5                   10                  15

Arg Arg Gln Leu Val His Phe Ala Trp Glu His Phe Arg Pro Arg Cys
            20                  25                  30

Lys Phe Val Trp Gly Pro Gln Asp Lys Leu Arg Arg Phe Lys Pro Ser
        35                  40                  45

Ser Leu
    50
```

METHODS AND COMPOSITIONS FOR TREATING CANCER

CROSS-REFERENCE TO RELATED APPLICATIONS

This application is a Continuation of U.S. application Ser. No. 16/928,830, filed Jul. 14, 2020, which claims priority to U.S. Provisional Application No. 62/874,037, filed Jul. 15, 2019, the disclosure of which is incorporated by reference in its entirety.

The instant application contains a Sequence Listing which has been submitted in ASCII format via EFS-WEB and is hereby incorporated by reference in its entirety. Said ASCII copy, created on Mar. 30, 2021, is named 126863-0105 SL.txt and is 1,913 bytes.

FIELD

The present invention relates to methods and compositions for treating cancer.

BACKGROUND

Cancer is a group of diseases involving abnormal cell growth with the potential to invade or spread to other parts of the body. In 2015, about 90.5 million people had cancer. About 14.1 million new cases occur each year (not including skin cancer other than melanoma), and cancer causes about 8.8 million deaths annually or about 15.7% of all deaths. Cancers are collectively the second leading cause of death in the United States today. The risk of cancer increases significantly with age, and many cancers occur more commonly in developed countries Cancer is thought to exhibit six characteristics that underlie the ability of cancer cells to form tumor and progress into a malignant state that allow the cells to propagate and invade other tissue than the originating tissue. These six characteristics are cell growth and division absent the proper signal, continuous growth and division even given contrary signals, avoidance of programmed cell death, limitless number of cell divisions, promoting blood vessel construction, invasion of tissue, and formation of metastases.

While our understanding of the characteristics of cancer has greatly improved, no fundamental trait or characteristic has been associated with the wide array of cancers known today which has permitted an effective uniform and successful treatment strategy for cancers. Cancer can be treated by surgery, chemotherapy, radiation therapy, hormonal therapy, and targeted therapy (including immunotherapy such as monoclonal antibody therapy). The choice of therapy depends upon the location and grade of the tumor and the stage of the disease, as well as the general state of the patient.

Despite a rapid increase in our understanding of the mechanisms underlying cancer development, many if not most cancers remain incurable, and there remain a great medical need for novel treatment strategies for cancer.

SUMMARY

One embodiment is a method of treating a cancer in a subject in need thereof, comprising locally administering an opioid growth factor receptor (OGFR) antagonist to a site in the subject containing cancer cells. In some embodiments, the OGFR antagonist comprises naloxone, naltrexone, a functional derivative or analog thereof, or a combination thereof. Another embodiment is a composition for use in a method of treating a cancer in a subject in need thereof, comprising locally administering an opioid growth factor receptor (OGFR) antagonist to a site in the subject containing cancer cells.

In some embodiments, the cancer comprises soft tissue non-osteogenic sarcomas, bone sarcomas, osteosarcoma, Ewing's sarcoma, chondrosarcoma, benign bone tumors, basal cell carcinoma, melanoma, thyroid adenocarcinomas, glial blastoma, pituitary tumors, oligodendrocytoma, bladder carcinoma, triple negative breast carcinoma, breast carcinoma, neuroblastoma, or astrocytoma. In some embodiments, the OGFR antagonist is administered at a local dosage of about 1 mM to about 10 mM.

In one aspect, the OGFR antagonist is administered locally by intratumoral injection.

In another aspect, OGFR antagonist is administered with a pharmaceutically acceptable carrier. In some embodiments, the pharmaceutically acceptable carrier comprises a collagen sponge, a powdered collagen, or a collagen based gelatin hydrogel. In some embodiments, the pharmaceutically acceptable carrier comprises a hydrogel based carrier. In one particular embodiment, the pharmaceutically acceptable carrier is a collagen sponge. In some embodiments, the hydrogel based carrier comprises a poly-(lactic acid)/poly-(ethylene glycol)/poly-(lactic acid) hydrogel, a poly-(ethylene glycol)/poly-(lactic acid)/poly-(ethylene glycol) hydrogel, or a combination thereof. In one particular embodiment, the hydrogel based carrier is poly-(ethylene glycol)/poly-(lactic acid)/poly-(ethylene glycol).

In some embodiments, the OGFR antagonist is administered with a diluent, wherein the diluent enhances the solubility of the OGFR antagonist. In some embodiments, the diluent comprises a polar organic solvent. Preferably, the polar organic solvent is dimethylsulfoxide (DMSO), including a DMSO-based saline solution. In another embodiment, the solubility-enhancing diluent is an acidified saline based solution, an alcohol, a polyol, alkane, fatty acid, ester, amine, amide, terpene, cyclodextrin, or surfactant. In one embodiment, the diluent comprises a dimethylsulfoxide (DMSO) based saline solution. In some embodiments, the DMSO based saline solution comprises from about 5% volume/volume (v/v) DMSO to about 80% v/v DMSO. In some embodiments, the DMSO based saline solution comprises about 50% v/v DMSO. In some embodiments, the acidified saline based solution exhibits a pH from about 4.5 to about 7.4.

BRIEF DESCRIPTION OF DRAWINGS

FIG. 3 depicts a spheroid assay showing that naloxone (an OGFR antagonist) treatment decreases tumor size in vitro.

FIG. 4 shows the effect of a naloxone formulation on tumor growth in mice implanted with MDA-MB-231 triple negative breast cancer cells. The formulation was implanted into the tibia of 8-week old female Cr nude mice.

DETAILED DESCRIPTION

Figure 1:
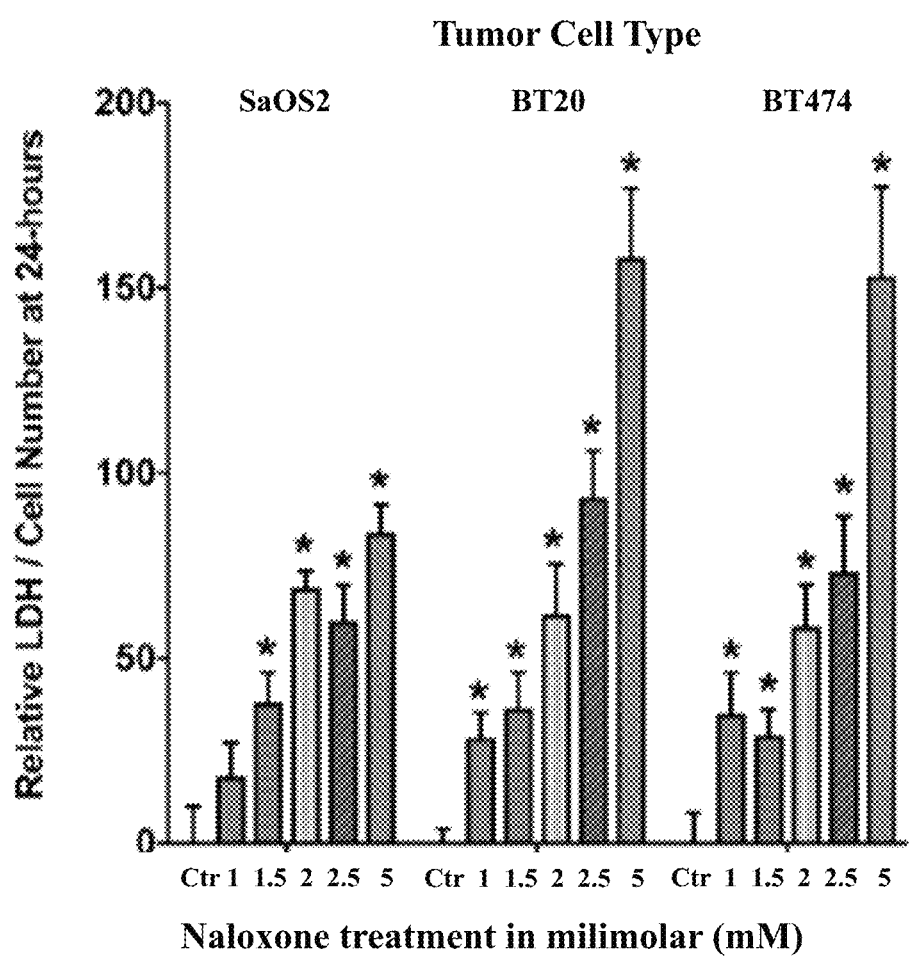
FIG. 1 depicts a graph showing expression of lactate dehydrogenase (LDH) upon naloxone, which is an Opioid Growth Factor Receptor (OGFR) antagonist, treatment of triple negative breast cancer cells (BT474), osteosarcoma cells (SaOS2, and breast cancer cells (BT20) compared to non-tumor cells. The expression of LDH is shown relative to LDH release upon naloxone treatment of non-tumor cells.

The disclosure herein is based on the surprising discovery that naloxone selectively induces cytotoxicity in tumor cells as compared to non-tumor cells. Accordingly, the present disclosure provides methods and compositions that are useful for inhibiting growth of tumor cells while sparing the surrounding normal cells. In some embodiments, the present disclosure provides methods and compositions for administering OGFR locally adjacent to the tumor or cancer cell in the patient.

The illustrative examples herein show that naloxone had a selective inhibitory effect on growth of osteosarcoma and breast cancer cells, including triple negative breast cancer cells. In some embodiments, naloxone treatment induced cytotoxicity selectively in tumor cells compared to corresponding non-tumor cells as determined by increased lactate dehydrogenase (LDH) expression. In some embodiments, naloxone induced a 6-fold increase in LDH expression relative to non-tumor cells in osteosarcoma cells and breast cancer cells. In some embodiments, naloxone induced a 3-fold increase in LDH expression in triple negative breast cancer cells. In some embodiments, naloxone treatment selectively inhibited cancer cell proliferation compared to non-cancer cells as determined by counting cell number after 72 hours of naloxone treatment. See FIGS. 1 and 2. In some embodiments, naloxone treatment reduced tumor growth of triple negative breast cancer cells as determined by a spheroid assay. See FIG. 3. In some embodiments, the naloxone formulation Nalovent™ reduced tumor growth in vivo when implanted adjacent to a tumor formed by triple negative breast cancer cells in mice. See FIG. 4.

Although the illustrative example demonstrated use of the methods and compositions disclosed herein for treating osteosarcoma and breast cancer, the present disclosure is contemplated to be useful for treating all types of cancer. Generally, cancer refers to a condition in which abnormal cells divide without control and can invade nearby tissues. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. In some embodiments, the cancer is one or more of pancreatic cancer, renal cancer, small cell lung cancer, brain cancer, neural cancer, bone cancer, lymphoma, myeloma, gastrointestinal tract cancer, uterine cancer, breast cancer, leukemia, liver cancer, prostate cancer, skin cancer, and melanoma. In some embodiments, the cancer is soft tissue non-osteogenic sarcomas, bone sarcomas, osteosarcoma, Ewing's sarcoma, chondrosarcoma, benign bone tumors, basal cell carcinoma, melanoma, thyroid adenocarcinomas, glial blastoma, pituitary tumors, oligodendrocytoma, bladder carcinoma, triple negative breast carcinoma, breast carcinoma, neuroblastoma, or astrocytoma.

Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other the ingredients and substantial method steps recited by the claims. Embodiments defined by each of these transition terms are within the scope of this invention.

As used here, the term "antagonist" is used interchangeably with "inhibitor" and refers to a substrate that blocks or suppresses the activity, function, effect, or expression of a target. In some embodiments, the target is a compound, a protein, a gene, a cell, or an agent. As used herein, the term "expression" refers to the amount a living cell produces of a target. In some embodiments, the inhibitor suppresses expression of a target gene or protein. In some embodiments, the inhibitor includes a compound that prevents binding of another molecule to an enzyme or molecular pump. In some embodiments, the inhibitor is a compound that causes downregulation of the enzyme. In some embodiments, the inhibitor can be a competing or non-competing inhibitor.

The term "administering" as used herein includes prescribing for administration as well as actually administering, and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The term "treating" or "treatment" covers the treatment of a cancer described herein, in a subject, such as a human, and includes (i) inhibiting a cancer, i.e., arresting its development; (ii) relieving a cancer or disorder, i.e., causing regression of the cancer; (iii) slowing progression of the cancer; and/or (iv) inhibiting, relieving, or slowing progression of one or more symptoms of the cancer. For example, treatment of a cancer includes, but is not limited to, elimination of the cancer or the condition caused by the cancer, remission of the tumor, inhibition of the cancer, or reduction or elimination of at least one symptom of the tumor.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar beginning compound by attaching another molecule or atom to the beginning compound. Further, derivatives, according to the invention, encompass one or more compounds formed from a precursor compound through addition of one or more atoms or molecules or through combining two or more precursor compounds.

Opioid Growth Factor Receptor (OGFR) Antagonists

By "Opioid Growth Factor Receptor (OGFR) antagonist" is meant any molecule that inhibits, suppresses or causes the cessation of at least one OGFR-mediated biological activity such as naloxone or a functional derivative thereof.

In some embodiments, an OGFR antagonist is an OGFR binding antagonist, namely, a molecule that, interferes with, blocks or otherwise prevents the interaction or binding of the met5-ligand (OGF) to the OGFR. Met-5 is derived from the pro-hormone pro-enkephalin (PENK).

An OGFR binding antagonist may compete with the met5-ligand for binding to the OGFR on the surface of the nuclear membrane, thereby interfering with, blocking or otherwise preventing the binding of the met5-ligand to the OGFR, without triggering the downstream signaling that would otherwise be induced by the binding of the met5-ligand to the OGFR. Alternatively, an OGFR binding antagonist may bind to or sequester pro-enkephalin (PENK) or the met5-ligand with sufficient affinity and specificity to substantially interfere with, block or otherwise prevent binding of met5-ligand to the OGFR, thereby inhibiting, suppressing or causing the cessation of at least one OGFR-mediated biological activity. Generally speaking, OGFR binding antagonists may be large molecules (e.g., antibodies) or small molecules (e.g., compounds of a molecular weight of less than 15-kD, 12-kD, 10-kDor even 8-kD), and may be a polypeptide, nucleic acid, or a synthetic small molecule compound. OGFR binding antagonists may be identified with any in vitro assay readily selected by one of skill in the art. For example, OGFR antagonists may be identified using the methods described in U.S. Pat. Nos. 5,882,944, 6,007,986, or U.S. Pat. No. 6,270,979.

In one embodiment, the OGFR binding antagonist is naloxone or a functional derivative thereof, naltrexone or a functional derivative thereof, or a combination thereof.

As used herein, a "functional derivative" refers to a derivative or analog that is structurally and functionally analogous to the originating molecule (e.g., maintains the function of naltrexone or naloxone as an OGFR antagonist). Naloxone and naltrexone analogs can be synthesized using standard synthetic procedures such as those described in March J., Advanced Organic Chemistry, 3rd Ed. (1985). Examples of naltrexone and naloxone functional derivatives include salt forms, e.g., naloxone hydrochloride dihydrate or naltrexone hydrochloride. Additional examples of naltrexone and naloxone functional derivatives suitable for use in the present methods include naltrexone and naloxone analogs disclosed in U.S. Patent Application Publication No. 2007/0197573 A1, U.S. Pat. No. 6,713,488, for example.

In another embodiment, an OGFR binding antagonist is derived from oxymorphone and binds to the OGFR, which includes naloxone, naltrexone, nalorphine, naloxonazine, levallorphan, nalmefene, cyprodime, cyclorphan, cyclazocine, oxilorphan, LY113878, MR2266, diprenorphine, WIN 44, 441-3, naltindole, or norbinaltorphimine.

In still another embodiment, an OGFR binding antagonist is derived from trans-3,4-dimethyl-4-phenylpiperidine and binds to the OGFR, which includes LY99335, LY25506, LY117413, or LY255582.

In another embodiment, an OGFR binding antagonist is derived from the met5-enkephalin or leu-enkephalin peptides, binds to the OGFR, and minimally includes the following amino acid sequences as a means of targeting the OGFR: Tyr-Gly-Gly-Phe-Met (SEQ ID NO: 1) for those derived from met5-enkephalin or Tyr-Gly-Gly-Phe-Leu (SEQ ID NO: 2) for those derived from the leu-enkephalin.

In still another embodiment, an OGFR binding antagonist is derived from the peptide antagonist 101174864 (N,N-diallyl-Tyr-Aib-Aib-Phe-Leu-OH, SEQ ID NO: 3; Aib=aminoisobutyticacid) or somatostatin analog CTP(D-Phe-Cys-Tyr-D-Trp-Lys-Thr-Pen-Thr-NH.sub.2, SEQ ID NO: 4).

In other embodiments, the OGFR antagonist, instead of being an OGFR binding antagonist, is a molecule that disrupts the nuclear localization sequence found within OGFR: 251 QSALDYFMFAVRCRHQRRQLVHFAWE-HFRPRCKFVWGPQDKLRRFKPSSL (SEQ ID NO: 5).

In still other embodiments, the OGFR antagonist employed in the present methods is a small-hairpin RNA (shRNA) or a small-interfering RNA (siRNA) directed against the OGFR gene and effective in disrupting OGFR gene expression.

The OGFR antagonists described herein can be administered individually or in combination. Suitable combinations include, for example, naloxone and naltrexone; naloxone and/or naltrexone, in combination with another OGFR binding antagonist or another OGFR antagonist.

Delivery Systems And Carriers For Local Administration

In one aspect of the present disclosure the OGFR antagonist is administered locally adjacent to the tumor site. In some embodiments, the OGFR antagonist is administered at a local dosage of about 1 µM to about 1 mM. In some embodiments, the OGFR antagonist is administered at a local dosage of about 1 mM to about 10 mM. In some embodiments, the local dosage is 1 mM, 1.5 mM, 2.0 mM, 3.0 mM, 4.0 mM, 5.0 mM, 6.0 mM, 7.0 mM, 8.0 mM, 9.0 mM, and/or 10.0 mM.

In some embodiments, the OGFR antagonist is administered with a carrier, and the carrier volume may be from about 0.1 cubic centimeter (cc) to about 20 cc, from about 0.25 cc to about 15 cc, from about 0.5 cc to about 10 cc, from about 1 cc to about 10 cc, from about 2 cc to about 10 cc. The corresponding amount of the OGFR antagonist in the carrier may be from about 0.2 mg per cc, 0.5 mg per cc, 1.0 mg per cc, 2.0 mg per cc, 3.0 mg per cc, 4.0 mg per cc, 5.0 mg per cc, 6.0 mg per cc, 7.0 mg per cc, 8.0 mg per cc, 9.0 mg per cc, and/or 10.0 mg per cc.

In some embodiments, the OGFR antagonist is administered locally by intratumoral injection.

In some embodiments, an OGFR antagonist is combined with or encapsulated within a carrier for administration.

Suitable carriers can be in bead, microsphere or nanoparticle form, and can be made of natural and/or synthetic biocompatible polymers. Examples of suitable biocompatible polymers include hyaluronic acid, collagen, tricalcium phosphate, chondroitin sulfate, polybutyrate, polylactide, polyglycolide, and lactide/glycolide copolymers, and mixtures or copolymers thereof. Suitable carriers also include on-polymer systems such as carboxylic acids, fatty acids, phospholipids, amino acids, lipids such as sterols, hydrogel release system; silastic system; peptide-based system; implants and the like.

In one embodiment, the carrier is a hygroscopic collagen based carrier such as a collagen sponge, a collagen scaffold, a powdered collagen, or a collagen based gelatin hydrogel.

In another embodiment, the carrier is a hydrophilic hydrogel based carrier (e.g., poly lactic acid, poly glycolic acid), which allows an OGFR antagonist (e.g., naloxone or naltrexone or a functional derivative thereof) infused therein to be released over a period of time.

In another embodiment, the carrier is a carrier composed of a tri-block co-polymer comprising a central block of PLA (poly-(lactic acid) flanked by two blocks of PEG-(poly-(ethylene glycol).

In still another embodiment, the carrier is albumin, a derivative or fragment of albumin that maintains the naloxone/morphine binding site located at the interface between the IA and IIA domains, and/or maintains the naloxone binding site around tryptophan (Trp)-214, that binds an OGFR antagonist such as naloxone or naltrexone or a functional derivative thereof and allows for a slow release of the OGFR antagonist.

In still another embodiment, methyl cellulose, and an inert gel, for example, that binds an OGFR antagonist such as naloxone or naltrexone or a functional derivative thereof and allows for a slow release of the antagonist.

In a further embodiment, the carrier is a bovine collagen implant. An OGFR antagonist, e.g., naloxone or naltrexone or a functional derivative thereof, can be combined with a bovine collagen implant, in a manner similar to either INFUSE (BMP2) or OP1 (osteogenic protein1 or BMP7)-putty or OP1-implant, that is supplied with a bovine collagen sponge, powdered bovine collagen, or collagen based gelatin construct. Administration of naloxone, naltrexone or a functional derivative thereof can be achieved by, e.g., reconstituting the powdered naloxone or naltrexone or a functional derivative thereof with sterile saline and then adding the OGFR antagonist-saline solution to the collagen implant; after which the implant can be delivered locally to the site of surgical intervention.

In a further embodiment, the carrier is composed of cement (polymethylmethacrylateor "PMMA"), or injectable formulations.

In another embodiment, the carrier is a carrier composed of PGA (poly-(glycolic acid)-PLGA (poly-(lactic glycolic acid)) spheres, which can encapsulate an OGFR antagonist to provide for immediate, delayed or sustained release.

Pharmaceutical Compositions And Administration

In some embodiments, a pharmaceutical composition disclosed herein comprises one or more "pharmaceutically acceptable carriers," such as an aqueous carrier, buffer, antioxidants, and/or diluents. In some embodiments, the pharmaceutical compositions comprise an OGFR antagonist in a dimethyl sulfoxide (DMSO) based saline solution. In some embodiments, the pharmaceutical compositions comprise more than about 100 mM of the OGFR antagonist in the dimethyl sulfoxide (DMSO) based saline solution In some embodiments, the pharmaceutical compositions comprises about 10 mM to about 150 mM of the OGFR antagonist in the dimethyl sulfoxide (DMSO) based saline solution. In some embodiments, the pharmaceutical compositions comprise about 20 mM to about 140 mM of the OGFR antagonist in the dimethyl sulfoxide (DMSO) based saline solution. In some embodiments, the pharmaceutical compositions comprise about 30 mM to about 130 mM of the OGFR antagonist in the dimethyl sulfoxide (DMSO) based saline solution. In some embodiments, the pharmaceutical compositions comprise about 40 mM to about 120 mM of the OGFR antagonist in the dimethyl sulfoxide (DMSO) based saline solution. In some embodiments, the pharmaceutical compositions comprise about 50 mM to about 110 mM of the OGFR antagonist in the dimethyl sulfoxide (DMSO) based saline solution. In some embodiments, the pharmaceutical compositions comprise about 50 mM to about 110 mM of the OGFR antagonist in the dimethyl sulfoxide (DMSO) based saline solution. In some embodiments, the pharmaceutical compositions comprise more than 100 mM of the OGFR antagonist in the dimethyl sulfoxide (DMSO) based saline solution. In some embodiments, the OGFR antagonist comprises about 100 mM naloxone, naltrexone, a functional derivative or analog thereof in the dimethyl sulfoxide (DMSO) based saline solution.

In some embodiments, the acidified saline based solution exhibits a pH from about 4.5 to about 7.4. In some embodiments, the acidified saline based solution exhibits a pH from about 5.5 to about 7.4. In some embodiments, the acidified saline based solution exhibits a pH from about 6.5 to about 7.4.

In some embodiments, the diluent is a dimethyl sulfoxide (DMSO) based saline solution. In some embodiments, the DMSO based saline solution comprises from about 1% volume/volume (v/v) DMSO to about 80% v/v DMSO. In some embodiments, the DMSO based saline solution comprises from about 5% volume/volume (v/v) DMSO to about 80% v/v DMSO. In some embodiments, the DMSO based saline solution comprises from about 10% volume/volume (v/v) DMSO to about 80% v/v DMSO. In some embodiments, the DMSO based saline solution comprises from about 15% volume/volume (v/v) DMSO to about 80% v/v DMSO. In some embodiments, the DMSO based saline solution comprises from about 25% volume/volume (v/v) DMSO to about 80% v/v DMSO. In some embodiments, the DMSO based saline solution comprises from about 30% volume/volume (v/v) DMSO to about 80% v/v DMSO. In some embodiments, the DMSO based saline solution comprises from about 35% volume/volume (v/v) DMSO to about 80% v/v DMSO. In some embodiments, the DMSO based saline solution comprises from about 40% volume/volume (v/v) DMSO to about 80% v/v DMSO. In some embodiments, the DMSO based saline solution comprises from about 40% volume/volume (v/v) DMSO to about 70% v/v DMSO.

In some embodiments, the DMSO based saline solution comprises about 1% volume/volume (v/v) DMSO. In some embodiments, the DMSO based saline solution comprises about 2% volume/volume (v/v) DMSO. In some embodiments, the DMSO based saline solution comprises about 3% volume/volume (v/v) DMSO. In some embodiments, the DMSO based saline solution comprises about 4% volume/volume (v/v) DMSO. In some embodiments, the DMSO based saline solution comprises about 5% volume/volume (v/v) DMSO. In some embodiments, the DMSO based saline solution comprises about 6% volume/volume (v/v) DMSO. In some embodiments, the DMSO based saline solution comprises about 7% volume/volume (v/v) DMSO. In some embodiments, the DMSO based saline solution comprises about 8% volume/volume (v/v) DMSO. In some embodiments, the DMSO based saline solution comprises about 9% volume/volume (v/v) DMSO. In some embodiments, the DMSO based saline solution comprises about 10% volume/volume (v/v) DMSO. In some embodiments, the DMSO based saline solution comprises about 20% volume/volume (v/v) DMSO. In some embodiments, the DMSO based saline solution comprises about 30% volume/volume (v/v) DMSO. In some embodiments, the DMSO based saline solution comprises about 40% volume/volume (v/v) DMSO. In some embodiments, the DMSO based saline solution comprises about 50% volume/volume (v/v) DMSO. In some embodiments, the DMSO based saline solution comprises about 60% volume/volume (v/v) DMSO. In some embodiments, the DMSO based saline solution comprises about 70% volume/volume (v/v) DMSO. In some embodiments, the DMSO based saline solution comprises about 80% volume/volume (v/v) DMSO.

In some embodiments, the dimethyl sulfoxide (DMSO) based saline solution comprises a phosphate buffered saline solution, a borate buffered saline solution, a Tris buffered saline solution, or a carbonate buffered saline solution.

In some embodiments, the saline solution comprises a salt and water. In some embodiments, the salt of the saline solution comprises sodium chloride, or potassium chloride. In some embodiments, the saline solution comprises from about 0.7% w/w salt to about 1.5% w/w salt. In some embodiments, the saline solution comprises about 0.7% salt. In some embodiments, the saline solution comprises about 0.8% salt. In some embodiments, the saline solution comprises about 0.9% salt. In some embodiments, the saline solution comprises about 1.0% salt. In some embodiments, the saline solution comprises about 1.1% salt. In some embodiments, the saline solution comprises about 1.2% salt. In some embodiments, the saline solution comprises about 1.3% salt. In some embodiments, the saline solution comprises about 1.4% salt. In some embodiments, the saline solution comprises about 1.5% salt.

The OGFR antagonist may be combined or coordinately administered with a suitable carrier or vehicle depending on the route of administration. The term "pharmaceutically acceptable carrier" refers to a carrier that is conventionally used in the art to facilitate the storage, administration, and/or the healing effect of an active agent of a pharmaceutical composition.

A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; cyclodextrins, including alpha-cyclodextrin, beta-cyclodextrin, and gamma-cyclodextrin; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents.

In some embodiments, the pharmaceutical composition comprises preservatives and antioxidants. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose such as Avicel™, PH101 microcrystalline cellulose and/or Avicel™, PH102 microcrystalline cellulose, and silicified microcrystalline cellulose such as ProSolv SMCC™. Suitable lubricants, including agents that act on the flow-ability of the powder to be compressed, may include colloidal silicon dioxide such as Aerosil® 200 (colloidal silicon dioxide), talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Monoammonium Glycyrrhizinate such as Magnasweet™ (a flavoring composition containing Monoammonium Glycyrrhizinate and trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention.

The pharmaceutical composition comprising an OGFR antagonist derivatives or salts thereof will be formulated and dosed in a fashion consistent with good medical practice, taking into account the clinical condition of the individual patient, the method of administration, the scheduling of administration, and other factors known to practitioners.

A variety of administration routes are available. The pharmaceutical composition of the invention may be practiced using any mode of administration that is medically acceptable, meaning any mode that produces effective levels of the active ingredients without causing clinically unacceptable adverse effects. Accordingly, the pharmaceutical compositions can be administered to a subject parenterally, orally, intraperitoneally, intravenously, intra-arterially, transdermally, sublingually, intramuscularly, rectally, transbuccally, intranasally, liposomally, via minicells, via antibody conjugation, via cell targeting peptides, via inhalation, vaginally, intraocularly, via local delivery by catheter or stent, subcutaneously, intra-adiposally, intra-articularly, or intrathecally.

Modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. Oral administration is used in prophylactic treatment because of the convenience to the patient as well as the dosing schedule.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's solution or fixed 25 oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Compositions suitable for oral administration may be presented as discrete units, such as capsules, tablets, or lozenges, each containing a predetermined amount of the active agent(s). Other compositions include suspensions in aqueous liquids or non-aqueous liquids such as a syrup, elixir, or an emulsion.

Other delivery systems can include time-release, delayed-release, or sustained-release delivery systems. Such systems can avoid repeated administrations of the pharmaceutical composition of this invention, increasing convenience to the subject and the physician. Many types of release delivery systems are available and known to those of ordinary skill in the art. They include polymer-based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in U.S. Pat. No. 5,075,109, for example. Delivery systems also include non-polymer systems that are: lipids, including sterols such as cholesterol, cholesterol esters, and fatty acids or neutral fats such as mono-, di-, and tri-glycerides; hydrogel release systems; sylastic systems; peptide-based systems; wax coatings; compressed tablets using conventional binders and excipients; partially fused implants; and the like.

The methods and compositions herein may be provided in the form of a kit. A "kit" is herein defined as a package and containing several individual parts that show a complementary effect when applied together. In this aspect, the effect achieved by a kit and the pharmaceutical composition are similar. The kit may optionally include instructions for using the pharmaceutical compositions.

The present invention is further illustrated by, though in no way limited to, the following examples.

Example 1—Naloxone Exhibits Selective Cytotoxic Effect on Tumor Cells Compared to Non-Tumor Cells The purpose of this experiment was to determine the anti-tumor growth activity of naloxone solubilized in an acidified saline solution with 50% (v/v) DMSO relative to other non-tumor cell phenotypes likely to be located adjacent to the tumor. The Naloxone formulation of this example is referenced herein as "Naloxone".

Figure 2:
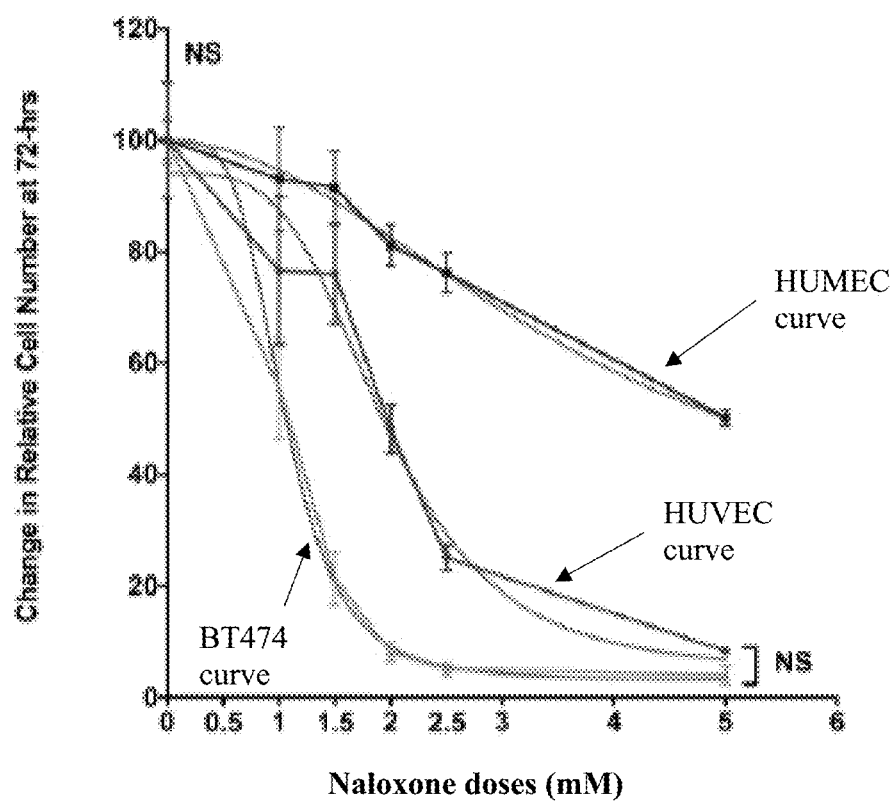
FIG. 2 depicts graphs showing changes in cell numbers of the triple negative breast cancer cells (BT474) compared to the normal non-tumor cells breast epithelium (HUMEC) and the normal vascular endothelium (HUVEC) cells as a function of increasing doses of naloxone.

The effect of the naloxone treatment at doses 1 mM, 1.5 mM, 2 mM, 2.5 mM, and 5 mM lactate dehydrogenase (LDH) on triple negative breast cancer cells (BT474), osteosarcoma cells (SaOS2, and breast cancer cells (BT20) was compared to the non-tumor cells breast epithelium (HUMEC) and the normal vascular endothelium (HUVEC) cells as shown in FIG. 1. Naloxone was added for 3 hours and LDH release was assessed at 24 hours post-treatment. At 24 hours, significant increase in LDH, corrected for changes in cell number caused by the treatment, was seen in triple negative breast cancer cells (BT474), osteosarcoma cells (SaOS2), and breast cancer cells (BT20) relative to the normal cells. As shown in FIG. 1, a 6-fold increase in LDH values was observed in SaOS2 and BT20 cells, and a 3-fold increase in cell LDH values was observed in BT474 (*p<0.001). At the highest dose, the cell number was decreased by 60% in the SaOS2 cells while BT20 and 90 cell numbers were decreased by 90% after 72 hours. See FIG. 2.

As seen in FIG. 1, exposure of triple negative breast cancer (TNBC) cells BT474 to for 72 h resulted in a significant reduction in the number of metabolically active cells compared to the control non-tumor cells, breast epithelium (HUMEC) or vascular endothelium (HUVEC) in a dose dependent manner. These data indicated that naloxone exhibits significant anti-tumor activity and may provide a non-tumor cell sparing effect up to the 2.5 mM dose.

Figures 3A, 3B, 3C:
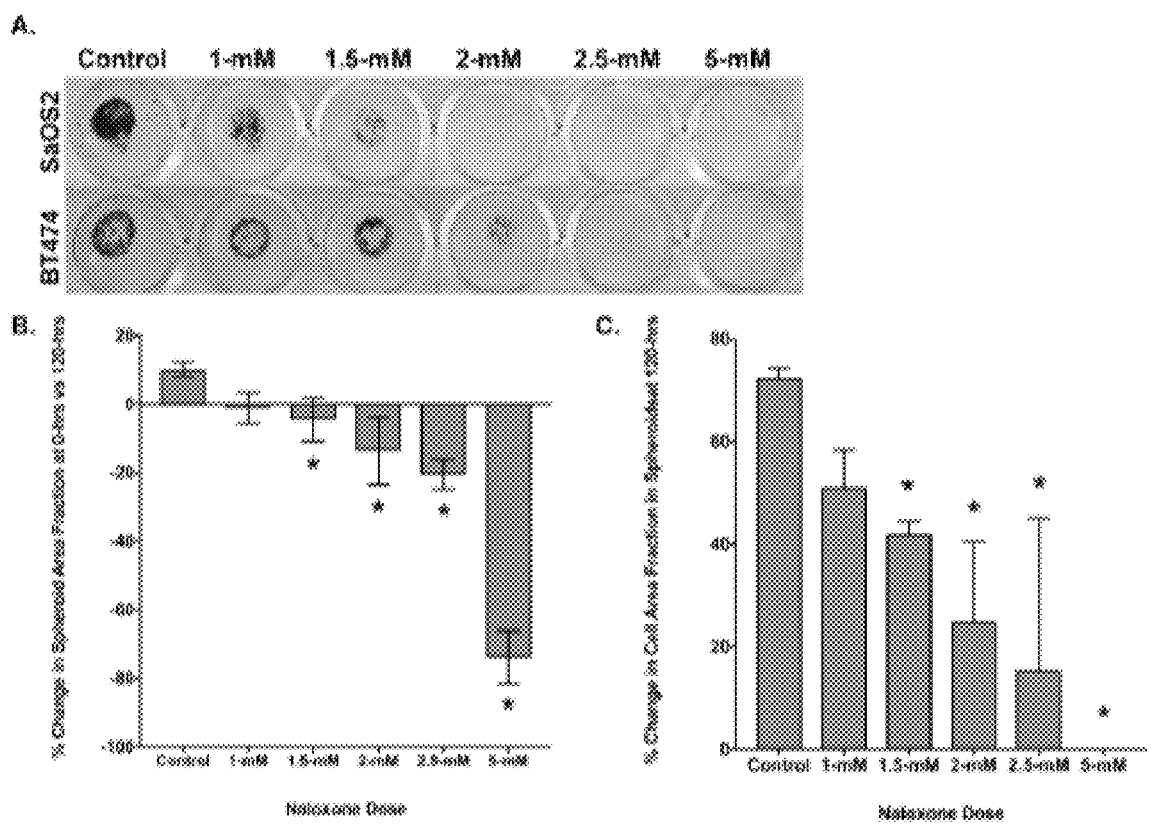
FIG. 3A shows the tumor spheroid formed with SaOS2 (osteosarcoma) and BT474 (triple negative breast cancer) cells in the presence of naloxone treatment at doses 1 mM, 1.5 mM, 2 mM, 2.5 mM, and 5 mM and no treatment control.
FIG. 3B depicts a graph showing quantification of the size of the spheroids formed in the spheroid assay described in FIG. 3A as percent change in spheroid area fraction between time 0 and 120 hours after treatment.
FIG. 3C depicts a graph showing quantification of the size of the spheroids formed in the spheroid assay described in FIG. 3A as percent change in cell area fraction in each spheroid at 120 hours after treatment.

It was also demonstrated that naloxone treatment decreased tumor size in vitro. Malignant tumors are characterized by invasion of surrounding normal tissues, and the spheroid assay is a simple micro-plate method (based on uniform, self-assembling 3D tumor spheroids) that is routinely used to assess tumor growth. The antitumor efficacy Naloxone was assessed using the spheroid assay, as shown in FIG. 3. The effects of anti-tumor efficacy were determined by quantifying the size of the spheroids formed in the and calculate percent change in spheroid area fraction between time 0 and 120 hours after treatment as shown in FIG. 3B. The anti-tumor efficacy was also determined by quantifying the percent change in cell area fraction in each spheroid at 120 hours after treatment as determined by staining the cells with crystal violet as shown in FIG. 3C. The results depicted in FIG. 3 showed that naloxone decreased the size of the tumor masses and the tumor mass cellularity in the SaOS2 osteosarcoma cells and the BT474 TNBC cells in a dose dependent manner.

Accordingly, the results herein showed that naloxone has a selective cytotoxic effect on tumor cells while sparing non-tumor cells. In addition, the results showed that naloxone can inhibit tumor cell growth in vitro.

Figure 4A:
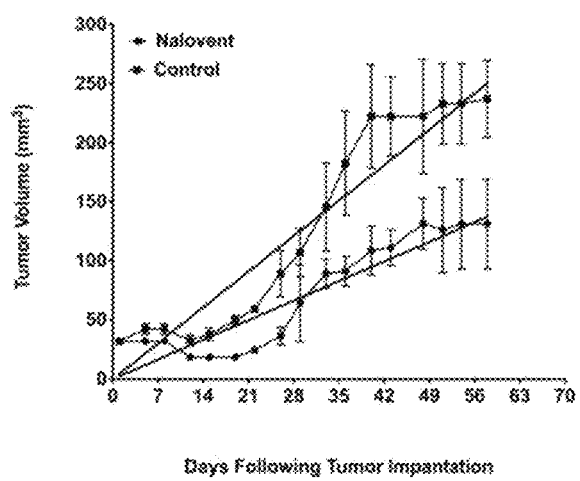
FIG. 4A shows that tumor caliper volumes were measured through 60 days. Tumor volumes were 2-fold smaller in the formulation implant group. A regression analysis found that the slope for the two treatment groups were significantly different ($p<0.001$).
Figure 4B:
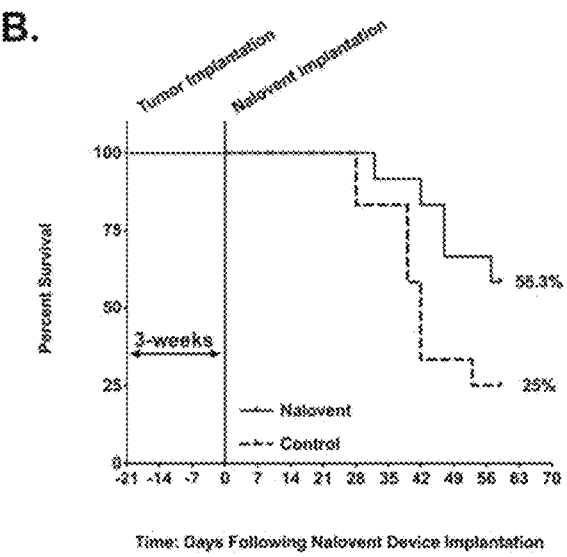
FIG. 4B shows an assessment of survival by using Kaplan-Meier statistic. The survival was 2-fold greater in the formulation treatment group ($p<0.0328$).

Example 2—this Example Shows that Local Administration of a Formulation of Approx. 50% DMSO in 0.9% Saline (50%) in a Collagen Sponge Adjacent to a Growing Tumor Effectively Inhibits in Vivo Tumor Growth and Increases Survival of Mice Inoculated with Breast Cancer To study the effect of this formulation on in vivo tumor growth, MDA-MB-231 triple negative breast cancer cells were implanted into female NCr nude mice. The formulation was implanted into the mice three weeks after the inoculation with MDA-MB-231 triple negative breast cancer cells in mice confirmed to actively growing tumors. The formulation was formulated by dissolving naloxone in an acidified saline solution with 50% (v/v) DMSO in a collagen gel based carrier. The formulation was implanted into the tibia of the 8-week old female NCr nude mice that had actively growing tumors formed by the implanted MDA-MB-231 triple negative breast cancer. FIG. 4 shows the effect of the formulation on tumor growth in mice implanted with MDA-MB-231 triple negative breast cancer cells. FIG. 4A shows that tumor caliper volumes were measured through 60 days. Tumor volumes were 2-fold smaller in the formulation implant group. A regression analysis found that the slope for the two treatment groups were significantly different (p<0.001). FIG. 4B shows an assessment of survival by using Kaplan-Meier statistic. The survival was 2-fold greater in the formulation treatment group (p<0.0328).

All references cited herein are specifically incorporated by reference in their entireties to the same extent as if individually incorporated. While preferred embodiments have been illustrated and described, it should be understood that changes and modifications can be made therein in accordance with ordinary skill in the art without departing from the invention in its broader aspects as defined herein.

Example 3—Local Injection of OGFR Antagonists Directly into the Tumor or Adjacent to the Tumor Inhibits Tumor Growth in Human Patients This example shows that delivering the OGFR antagonists directly into or adjacent to tumors may inhibit tumor growth in human patients suffering from a cancer.

The OGFR antagonist is administered to a human patient suffering a cancer such as breast cancer, liver cancer, lung cancer, skin cancer, brain cancer, or prostate cancer. The OGFR antagonist is administered as a pharmaceutical formulation of naloxone, dimethyl sulfide, saline, pharmaceutically acceptable excipients, and a hydrogel based carrier as described herein. The volume of the pharmaceutical formulation is between 0.25 cubic centimeter (cc) and 10 cc or between 10% and 150% of the tumor volume. The dose of the OGFR antagonist naloxone is from 2 milligram (mg) per cc of the carrier to about 8 mg per cc of the carrier. In particular, the dose of the OGFR antagonist naloxone is 2 mg per cc of the carrier, 4 mg per cc of the carrier, or it is 8 mg per cc of carrier. The volume of carrier and amount of OGFR antagonist will vary depending on type of cancer and mode of delivery as illustrated below.

For some patients, the pharmaceutical formulation containing the OGFR antagonist is adapted for injection. The injectable OGFR antagonist composition is injected directly into the solid primary or metastatic tumor. For some patients suffering from lung cancer, the pharmaceutical formulation containing the OGFR antagonist is adapted for inhalation, and the pharmaceutical formulation containing the OGFR antagonist is delivered via inhalation.

In a liver patient, the pharmaceutical formulation containing the OGFR antagonist is injected into the viscera and deep tissue of the liver of the patient suffering from liver cancer by using fluoroscopy guided injection. Alternatively, for treating a patient with liver cancer, the pharmaceutical formulation containing the OGFR antagonist is delivered to the tumor through local perfusion via a catheter. In addition, the liver tumor is removed and the pharmaceutical formulation containing the OGFR antagonist is delivered into the adjacent tissue bed at the tumor site to control tumor recurrence.

The pharmaceutical formulation containing the OGFR antagonist is also used to treat lung cancer. The pharmaceutical formulation containing the OGFR antagonist is injected into the viscera and deep tissue of the lung of a patient suffering from lung cancer. Hence, in a patient with lung cancer, the pharmaceutical formulation containing the OGFR antagonist is injected directly into or adjacent to the tumor during tumor resection or lobectomy. The pharmaceutical formulation containing the OGFR antagonist is in some cases adapted for inhalation and delivered to the patient suffering from lung cancer via inhalation.

In a patient with brain tumor, the pharmaceutical formulation containing the OGFR antagonist is injected during tumor resection or is administered via a port or catheter prior to or following tumor resection.

The pharmaceutical formulation containing the OGFR antagonist is also used to treat skin cancer. The pharmaceutical formulation containing the OGFR antagonist is injected into the skin tumor or adjacent to the skin tumor to treat the patient suffering from skin cancer. In a patent where the tumor is a skin tumor located on the skin, the skin tumor is treated through scraping of the tumor or tumor resection, and then the pharmaceutical formulation containing the OGFR antagonist is delivered locally via conventional means (i.e. hand placement and or hand packing into the resection) that do not include injection. During incisional biopsy or partial resection of a skin tumor such as melanoma or squamous cell carcinoma or basal cell carcinoma, the pharmaceutical formulation containing the OGFR antagonist is injected into the resection space and/or adjacent to the tumor. For treating skin cancer, the volume of the pharmaceutical composition containing the OGFR antagonist is between 0.25 cc and 2.5 cc or between 10% and 150% of the tumor volume. The dose of the OGFR antagonist naloxone is from 2 milligram (mg) per cc of the carrier to about 8 mg per cc of the carrier. For one patient suffering from skin cancer, the corresponding dose of the OGFR antagonist naloxone is 2 mg per cc of the carrier. In another skin cancer patient, the corresponding dose of the OGFR antagonist naloxone is 4 mg per cc of the carrier. In another skin cancer patient, corresponding dose of the OGFR antagonist naloxone is 8 mg per cc of carrier.

For treating a breast tumor, the pharmaceutical formulation containing the OGFR antagonist is delivered directly into the breast tumor during a wire localization or needle localization procedure (i.e. stereotactic wire localization), in which a mammogram or ultrasound is used to guide a thin hollow needle to the tumor. In this procedure some breast tissue is removed for biopsy and then a second needle containing the preferred formulation is injected into and adjacent to the tumor mass. For treating breast cancer, the volume of the pharmaceutical composition containing the OGFR antagonist is between 1 cc and 10 cc or between 10% and 150% of the tumor volume. The dose of the OGFR antagonist naloxone is from 2 milligram (mg) per cc of the carder to about 8 mg per cc of the carrier. For one patient suffering from breast cancer, the corresponding dose of the OGFR antagonist naloxone is 2 mg per cc of the carrier. In another breast cancer patient, the corresponding dose of the OGFR antagonist naloxone is 4 mg per cc of the carrier. In another skin cancer patient, the corresponding dose of the OGFR antagonist naloxone is 8 mg per cc of earlier.

What is claimed is:

1. A method of treating a breast cancer in a subject in need thereof, comprising locally administering a composition comprising (a) at least about 1 mM of an opioid growth factor receptor (OGFR) antagonist selected from the group consisting of naloxone, naltrexone, a functional derivative or analog thereof, and a combination thereof, and (b) a diluent comprising an acidified DMSO based saline solution, to a site in the subject containing a breast cancer tumor.

2. The method of claim 1, wherein the cancer comprises triple negative breast carcinoma.

3. The method of claim 1, wherein the OGFR antagonist is administered locally by intratumoral injection.

4. The method of claim 1, wherein the OGFR antagonist is administered with a pharmaceutically acceptable carrier.

5. The method of claim 4, wherein the pharmaceutically acceptable carrier comprises a collagen based carrier in the form of a collagen sponge, a powdered collagen, or a collagen based gelatin hydrogel.

6. The method of claim 5, wherein the pharmaceutically acceptable carrier is the collagen sponge.

7. The method of claim 4, wherein the pharmaceutically acceptable carrier comprises a hydrogel based carrier.

8. The method of claim 7, wherein the hydrogel based carrier comprises a poly-(lactic acid)/poly-(ethylene glycol)/poly-(lactic acid) hydrogel, a poly-(ethylene glycol)/poly-(lactic acid)/poly-(ethylene glycol) hydrogel, or a combination thereof.

9. The method of claim 8, wherein the hydrogel based carrier is poly-(ethylene glycol)/poly-(lactic acid)/poly-(ethylene glycol).

10. The method claim 1, wherein the acidified DMSO based saline solution comprises from about 1% volume/volume (v/v) DMSO to about 80% v/v DMSO.

11. The method of claim 1, wherein the acidified DMSO based saline solution comprises about 50% v/v DMSO.

12. The method of claim 1, wherein the OGFR antagonist is naloxone and the diluent increases the solubility of naloxone up to about 150 mM.

13. The method of claim 1, wherein the volume of the composition is between 10% and 150% of the tumor volume.

14. The method of claim 1, wherein the composition comprises from 10 mM to 150 mM of the OGFR antagonist.

15. The method of claim 1, wherein the composition comprises from 20 mM to 140 mM of the OGFR antagonist.

16. The method of claim 1, wherein the composition comprises from 30 mM to 130 mM of the OGFR antagonist.

17. The method of claim 1, wherein the composition comprises from 40 mM to 120 mM of the OGFR antagonist.

18. The method of claim 1, wherein the composition comprises from 50 mM to 110 mM of the OGFR antagonist.

19. The method of claim 1, wherein the composition comprises more than 100 mM of the OGFR antagonist.

20. The method of claim 1, wherein the OGFR antagonist is naloxone.

* * * * *